(12) United States Patent
Ma et al.

(10) Patent No.: US 11,678,826 B2
(45) Date of Patent: Jun. 20, 2023

(54) MAGNETOMETER USED FOR CARDIAC MAGNETIC FIELD MEASUREMENT AND BASED ON NITROGEN-VACANCY (NV) CENTERS IN DIAMOND, AND CARDIAC MAGNETIC FIELD MEASUREMENT SYSTEM

(71) Applicant: North University of China, Taiyuan (CN)

(72) Inventors: Zongmin Ma, Taiyuan (CN); Jun Liu, Taiyuan (CN); Li Qin, Taiyuan (CN); Xiaoming Zhang, Taiyuan (CN); Doudou Zheng, Taiyuan (CN); Yunbo Shi, Taiyuan (CN); Jun Tang, Taiyuan (CN); Hao Guo, Taiyuan (CN); Xiaocheng Wang, Taiyuan (CN)

(73) Assignee: North Univeristy of China, Taiyuan (CN)

( * ) Notice: Subject to any disclaimer, the term of this patent is extended or adjusted under 35 U.S.C. 154(b) by 255 days.

(21) Appl. No.: 17/327,671

(22) Filed: May 22, 2021

(65) Prior Publication Data

US 2021/0378569 A1 Dec. 9, 2021

(30) Foreign Application Priority Data

Jun. 3, 2020 (CN) .......................... 202010491935.X (51) Int. Cl.
| | | |
|---|---|---|
| *A61B 5/05* | (2021.01) | |
| *A61B 5/243* | (2021.01) | |
| *A61B 5/00* | (2006.01) | |
| *G01N 21/64* | (2006.01) | |

(52) U.S. Cl.
CPC ............ *A61B 5/243* (2021.01); *A61B 5/0071* (2013.01); *G01N 21/6428* (2013.01)

(58) Field of Classification Search
CPC ....... A61B 5/0071; A61B 5/055; A61B 5/243; G01N 21/6428
See application file for complete search history.

*Primary Examiner* — Mark D Remaly
(74) *Attorney, Agent, or Firm* — Hickman Becker Bingham Ledesma LLP (57) ABSTRACT

The present disclosure provides a cuboid magnetometer with high fluorescence collection efficiency, used for cardiac magnetic field measurement, and based on nitrogen-vacancy (NV) centers in diamond, and a cardiac magnetic field measurement system. The cardiac magnetic field measurement system includes a magnetic shielding chamber, a non-magnetic bed, an array probe for cardiac magnetic field measurement, a three-axis displacement platform, a high-speed data collection card, a fiber laser source, a microwave source, and a computer. The array probe for cardiac magnetic field measurement includes a non-magnetic shell, a stepping motor, a porous rotary fiber coupling apparatus, a fiber bundle set, a special photodetector (PD) set, a filter set, a ring-shaped antenna, and special diamond.

10 Claims, 5 Drawing Sheets

MAGNETOMETER USED FOR CARDIAC MAGNETIC FIELD MEASUREMENT AND BASED ON NITROGEN-VACANCY (NV) CENTERS IN DIAMOND, AND CARDIAC MAGNETIC FIELD MEASUREMENT SYSTEM

RELATED APPLICATION

This application claims priority under 35 U.S.C. 119(a)-(d) to China Application No. 202010491935.X entitled "MAGNETOMETER USED FOR CARDIAC MAGNETIC FIELD MEASUREMENT AND BASED ON NITROGEN-VACANCY (NV) CENTERS IN DIAMOND, AND CARDIAC MAGNETIC FIELD MEASUREMENT SYSTEM" and filed in China on Jun. 3, 2020, the contents of which are herein incorporated in their entirely by reference for all purposes.

TECHNICAL FIELD

The present disclosure relates to the field of biomedical instruments, and specifically, to a magnetometer used for cardiac magnetic field measurement and based on nitrogen-vacancy (NV) centers in diamond, and a cardiac magnetic field measurement system.

BACKGROUND

A magnetocardiogram (MCG) is of great significance in clinical diagnosis, and is widely used to diagnose and monitor arrhythmia, myocardial ischemia with coronary heart disease, hypertensive left ventricular hypertrophy, fetal myocardial hypertrophy, and the like. The MCG has outstanding advantages in heart disease risk classification, general survey, effect evaluation of interventional diagnosis and treatment, positioning of accessory pathways in wolff-parkinson-white syndrome, and the like.

A superconducting quantum interference device (SQUID) system is currently used in the medical field. Although sensitivity of the SQUID system at low temperature can reach 10 fT, which is enough for cardiac magnetic field measurement, the SQUID system must work in an ultra-low temperature environment. At present, a Dewar bottle filled with liquid helium is used for cooling. The liquid helium will volatilize when being used, so the expensive liquid helium must be continuously replenished. This results in higher operation and maintenance costs of the SQUID system. Moreover, because of the low temperature environment and a relatively fixed structure of the SQUID system, the SQUID system cannot be in contact with the skin for cardiac magnetic field measurement.

At present, a magnetometer based on NV centers in diamond has achieved a sensitivity of an aT level. In addition, different from the SQUID system, the magnetometer does not need a liquid nitrogen environment. Moreover, the magnetometer based on the NV centers in the diamond is developing towards integration and miniaturization, and has a wide application prospect. Therefore, it is possible to produce a new magnetocardiography system that has high sensitivity and low costs, and supports contact measurement.

SUMMARY

To overcome the disadvantages in the prior art, the present disclosure provides a magnetometer used for cardiac magnetic field measurement and based on NV centers in diamond, and a cardiac magnetic field measurement system. The cardiac magnetic field measurement system features low maintenance costs, high sensitivity, and strong adjustability, and becomes a new-generation magnetocardiography system with high precision, high efficiency, and low costs.

In some embodiments, a magnetometer used for cardiac magnetic field measurement and based on NV centers in diamond includes an array probe for cardiac magnetic field measurement, a fiber laser source, and a microwave source. The array probe for cardiac magnetic field measurement includes a non-magnetic shell, a stepping motor, a porous rotary fiber coupling apparatus, a fiber bundle set, a special photodetector (PD) set, a filter set, a ring-shaped antenna, and special diamond.

In some embodiments, the porous rotary fiber coupling apparatus includes a rotating disk and a chassis. The rotating disk is made of a non-magnetic material, and is provided with a laser through hole for connecting to a laser fiber, and the rotating disk is connected to an output shaft of the stepping motor. The chassis is made of the non-magnetic material, and is provided with m through holes that form a circle. The m through holes are equally spaced, positions of the through holes correspond to a position of the laser through hole on the rotating disk, and the m through holes each are used to connect to one end of one of m fibers in the fiber bundle set. After the probe is secured, the porous rotary fiber coupling apparatus is configured to drive, by using the stepping motor, the rotating disk to rotate periodically. A laser source fiber in the through hole is in contact with the fiber in the through hole to couple the laser source fiber with different fiber bundles. In this way, m small unit blocks of the special diamond can excite measurement for magnetic fields at corresponding positions in turn, to finally achieve a scanning detection effect after the probe is secured. The special diamond is a block-shaped diamond, and is divided into a total of m small unit blocks. A layer of coating is covered on a front surface of the special diamond, and a hole is formed in the center of each small unit block, so that the center of each small unit block is injected with nitrogen atoms to produce NV centers. The special PD set is tightly distributed on surfaces of the special diamond. The PD attached on the front surface of the special diamond is provided with m holes, and each hole corresponds to one nitrogen atom injection position in the special diamond. The other end of each of the m fibers is connected to one of the m small unit blocks through one of the m holes on the front PD. The ring-shaped antenna is attached on a surface of one of the other PDs. The special diamond emits 600 nm-800 nm fluorescence under the irradiation of 532 nm laser. The ring-shaped antenna is connected to the microwave source to evenly radiate electromagnetic waves, so that the Optical Detected Magnetic Resonance (ODMR) signal is performed together with the function of magnetic field. The PDs are attached on various surfaces of the special diamond to wrap the special diamond, and are configured to collect and absorb all the fluorescence excited by the special diamond, to greatly improve collection efficiency, convert a collected light signal into an electrical signal, and send the electrical signal.

In some embodiments, with the magnetometer used for cardiac magnetic field measurement and based on NV centers in diamond, the array probe for cardiac magnetic field measurement further includes a filter set. A surface, in contact with the special diamond, of each PD in the special PD set is attached with a filter, and a front filter is also provided with m holes. The filter is attached on the surface close to the special diamond to pass light within the wavelength of 600-800 nm, so that the PD only collects the 600-800 nm fluorescence.

In some embodiments, with the magnetometer for cardiac magnetic field measurement and based on NV centers in diamond, each small unit block of the special diamond is provided with a fiber collimator, and the other end of each of the m fibers is connected to the fiber collimator to align laser light at the NV center of each small unit block.

In some embodiments, with the magnetometer used for cardiac magnetic field measurement and based on NV centers in diamond, the fiber collimator is provided with a convex lens. The convex lens performs focusing to increase strength of the laser light in a unit area, to improve excitation strength of the NV centers in the special diamond, thereby improving a measurement effect.

In some embodiments, with the magnetometer used for cardiac magnetic field measurement and based on NV centers in diamond, a bottom surface of the rotating disk is provided with a convex point, and a top surface of the chassis is provided with a concave point matching the convex point.

In some embodiments, a cardiac magnetic field measurement system includes a three-axis displacement platform, a non-magnetic bed, a magnetic shielding chamber, a high-speed data collection card, and a computer. The system further includes the foregoing magnetometer. The special PD set in the magnetometer is connected to the high-speed data collection card, and the high-speed data collection card is connected to the computer. An electrical signal of the PD is transmitted to the high-speed data collection card, and then transmitted to the computer by the high-speed data collection card. Finally, the computer performs data processing, simulates, analyzes, amplifies, and filters the collected electrical signal, and then obtains a strength diagram of a measured cardiac magnetic field by drawing, based on strength of an electrical signal measured in each position and the corresponding position, the electrical signal in each position in the computer.

In some embodiments, the NV centers in the special diamond generate the 600-800 nm fluorescence under the 532 nm laser light. If there is a magnetic field (cardiac magnetic field) nearby, Zeeman splitting occurs. Under these conditions, the ODMR signal is generated on the condition that the NV centers received an electromagnetic wave by using the microwave antenna, and the sweeping frequency of microwave including to the Zeman splitting. Strength of the magnetic field (cardiac magnetic field) is determined based on splitting strength. The entire process may be performed under room temperature. Therefore, liquid nitrogen-based refrigeration in a SQUID system can be abandoned to reduce costs. In addition, a device with room temperature can be in contact with the skin for measurement, so that better accuracy can be achieved. The special diamond with a mask injected and the porous rotary fiber coupling apparatus can be used to perform scanning measurement without moving the probe, to improve the accuracy. The PDs are attached on various surfaces of the special diamond to wrap the special diamond, and are configured to collect and absorb all the fluorescence excited by the special diamond, to greatly improve collection efficiency, convert a collected light signal into an electrical signal, and send the electrical signal to the high-speed data collection card. Then the high-speed data collection card transmits the electrical signal to the computer. Finally, the computer performs data processing, simulates, analyzes, amplifies, and filters the collected electrical signal, and then obtains a strength diagram of a measured cardiac magnetic field by drawing, based on strength of an electrical signal measured in each position and the corresponding position, the electrical signal in each position in the computer.

The system disclosed in this application has the following beneficial effects:

(1) A traditional magnetocardiography based on the SQUID system works in a low temperature environment, and needs to be cooled by using the liquid helium. The liquid helium is expensive, and will evaporate continuously when being used. Therefore, the traditional magnetocardiography has high operation and maintenance costs. However, the magnetometer used for cardiac magnetic field measurement and based on NV centers in diamond, and the MCG generation system do not need to be cooled by using the liquid helium, and therefore, have low operation and maintenance costs.

(2) The probe of the traditional SQUID system cannot be in contact with the human body because of the cooling system, and the strength of the magnetic field is inversely proportional to the square of a distance. Therefore, a signal measured by the probe in the cardio magnetic field is weak. However, in a magnetocardiography system of the magnetometer based on NV centers in diamond, an array for multi-channel cardiac magnetic field measurement can realize contact measurement. Therefore, a measured signal has a higher signal-to-noise ratio, and a measurement result is more accurate.

(3) The traditional SQUID system has a fixed structure, and cannot adapt to different individuals well. In addition, the traditional SQUID system is bulky and heavy, and cannot be inconveniently used. However, a single magnetometer based on NV centers in diamond is small, and still has room for miniaturization. The magnetometer supports personalized array layouts for different individuals, and has more advantages in future application.

(4) The porous rotary fiber coupling apparatus adjusts an optical path by rotating a coupling hole, and this reduces probe translations and improves relative precision and detection efficiency.

(5) The fluorescence collection apparatuses on the six surfaces of the special diamond can collect almost all fluorescence except fluorescence at an opening of the porous PD. In this way, the fluorescence collection efficiency theoretically approximates 100%. The high collection efficiency leas to more accurate and effective detection.

DESCRIPTION OF REFERENCE NUMERALS

1 represents an array probe for cardiac magnetic field measurement, 2 represents a three-axis displacement platform, 3 represents a non-magnetic bed, 4 represents a magnetic shielding chamber, 5 represents a high-speed data collection card, 6 represents a fiber laser source, 7 represents a microwave source, and 8 represents a computer.

1-1 represents a non-magnetic shell, 1-2 represents a stepping motor, 1-3 represents a rotating disk, 1-4 represents a chassis, 1-5 represents a fiber bundle set, 1-6 represents a special PD set, 1-7 represents a filter set, 1-8 represents a ring-shaped antenna, and 1-9 represents special diamond.

1-3-1 represents a laser through hole.

1-4-1 represents a through hole.

1-5-1 represents a fiber collimator, and 1-5-2 represents a convex lens.

1-6-1 represents a porous PD (8 mm*8 mm), 1-6-2 represents a PD (8 mm*1 mm) on a left surface of the special PD set, 1-6-3 represents a PD (8 mm*1 mm) on a front surface of the special PD set, 1-6-4 represents a PD (8 mm*8 mm) on a bottom surface of the special PD set, 1-6-5 represents a PD (8 mm*1 mm) on a right surface of the special PD set, and 1-6-6 represents a PD (8 mm*1 mm) on a rear surface of the special PD set.

1-9-1 represents a small unit block (1 mm*1 mm*1 mm), and 1-9-2 represents NV centers in diamond.

DETAILED DESCRIPTION

In the following, embodiments of the present disclosure will be described in detail. Details of certain technical solutions are provided, but the protection scope of the present disclosure is not limited to the following embodiments.

Figure 1:
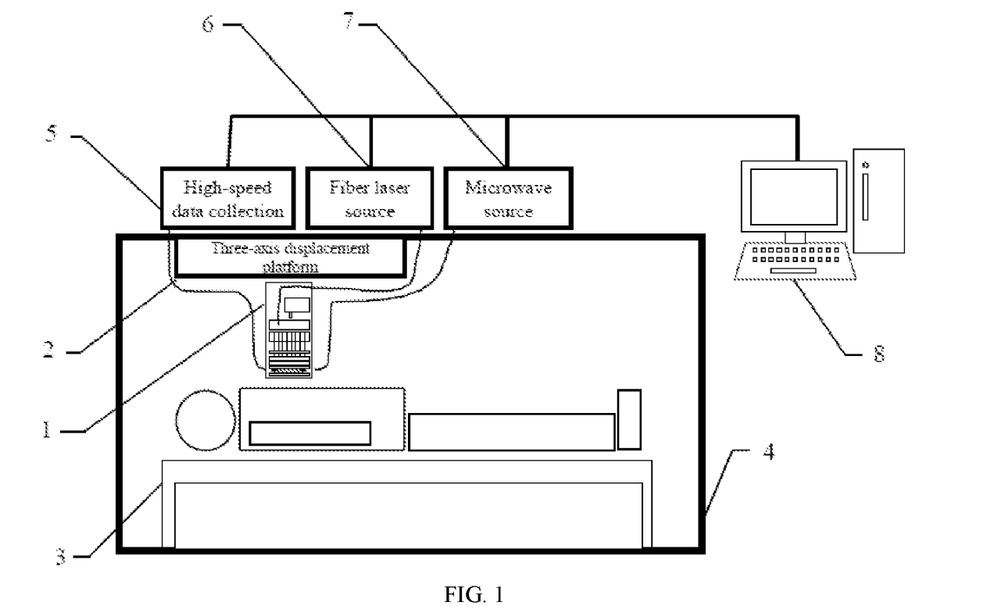
FIG. 1 is a schematic diagram illustrating a cuboid magnetometer with high fluorescence collection efficiency, used for cardiac magnetic field measurement, and based on NV centers in diamond, and a cardiac magnetic field measurement system according to embodiments of the present disclosure.

In reference to FIG. 1, the present disclosure provides a cuboid magnetometer with high fluorescence collection efficiency, used for cardiac magnetic field measurement, and based on NV centers in diamond, and a cardiac magnetic field measurement system. The apparatus includes an array probe 1 for cardiac magnetic field measurement, a three-axis displacement platform 2, a non-magnetic bed 3, a magnetic shielding chamber 4, a high-speed data collection card 5, a fiber laser source 6, a microwave source 7, and a computer 8.

Figure 2:
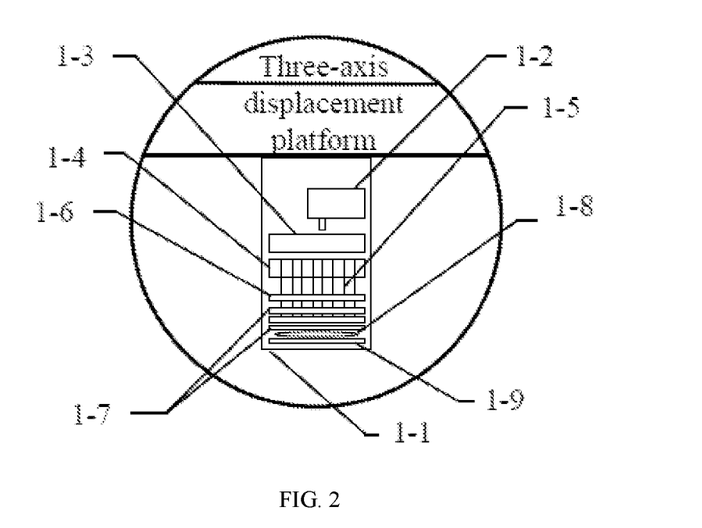
FIG. 2 is a schematic structural diagram illustrating an array probe for cardiac magnetic field measurement.

In reference to FIG. 2, the array probe 1 for cardiac magnetic field measurement includes a non-magnetic shell 1-1, a stepping motor 1-2, a porous rotary fiber coupling apparatus, a fiber bundle set 1-5, a special PD set 1-6, a filter set 1-7, a ring-shaped antenna 1-8, and special diamond 1-9. The porous rotary fiber coupling apparatus includes a rotating disk 1-3 and a chassis 1-4. The stepping motor 1-2, the porous rotary fiber coupling apparatus, the fiber bundle set 1-5, the special PD set 1-6, the filter set 1-7, the ring-shaped antenna 1-8, and the special diamond 1-9 are all located in the non-magnetic shell 1-1, and the stepping motor 1-2 is located at the top. The rotating disk 1-3 is connected to an output shaft of the stepping motor 1-2. In the non-magnetic shell 1-1, bayonets are provided at corresponding positions of the stepping motor 1-2, the chassis 1-4, the special PD set 1-6, and the special diamond 1-9, to secure internal devices so that relative positions of the internal devices do not change.

Figure 3:
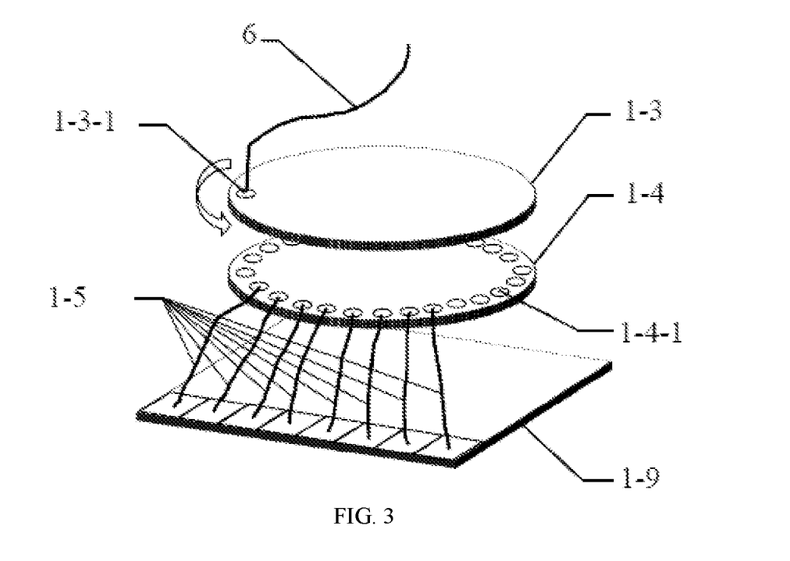
FIG. 3 is a schematic structural diagram illustrating a porous rotary fiber coupling apparatus.

In reference to FIG. 3, the porous rotary fiber coupling apparatus includes the rotating disk 1-3 and the chassis 1-4. The rotating disk 1-3 is made of a non-magnetic material, and is provided with a laser through hole 1-3-1 for connecting to a laser fiber, and the rotating disk 1-3 is connected to the output shaft of the stepping motor 1-2. The chassis 1-4 is also made of the non-magnetic material, and is provided with 64 through holes 1-4-1 that form a circle. The 64 through holes 1-4-1 are equally spaced, positions of the through holes 1-4-1 correspond to a position of the laser through hole 1-3-1 on the rotating disk 1-3, and the 64 through holes 1-4-1 are used to connect to 64 fibers in the fiber bundle set 1-5. The rotating disk 1-3 and the chassis 1-4 are provided with a concave point and a convex point respectively to secure relative positions after rotation, to improve stability. After the probe is secured, the porous rotary fiber coupling apparatus is configured to drive, by using the stepping motor 1-2, the rotating disk 1-3 to rotate periodically. A laser source fiber in the through hole 1-3-1 is in contact with the fiber in the through hole 1-4-1 to couple the laser source fiber with different fiber bundles. In this way, a total of 64 small unit blocks of the special diamond 1-9 can excite measurement for magnetic fields at corresponding positions in turn, to finally achieve a scanning detection effect after the probe is secured.

Figure 4:
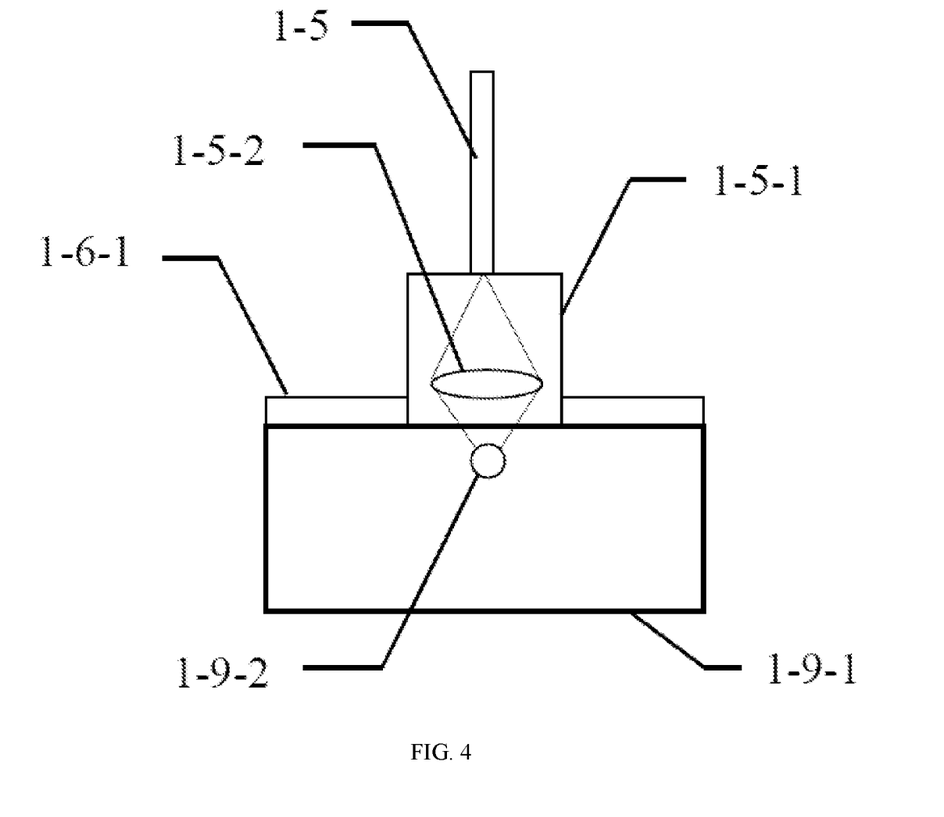
FIG. 4 is a schematic structural diagram illustrating a connection between a fiber bundle set and diamond.

In reference to FIG. 4, each small unit block 1-9-1 of the special diamond is provided with a fiber collimator 1-5-1. Each fiber in the fiber bundle set 1-5 is connected to the fiber collimator 1-5-1. The fiber collimator 1-5-1 is provided with a convex lens 1-5-2 to align laser light at NV centers 1-9-2 of each small unit block. In addition, the convex lens 1-5-2 performs focusing to increase strength of the laser light in a unit area, to improve excitation strength of the NV centers 1-9-2 in the special diamond, thereby improving a measurement effect.

Figure 5:
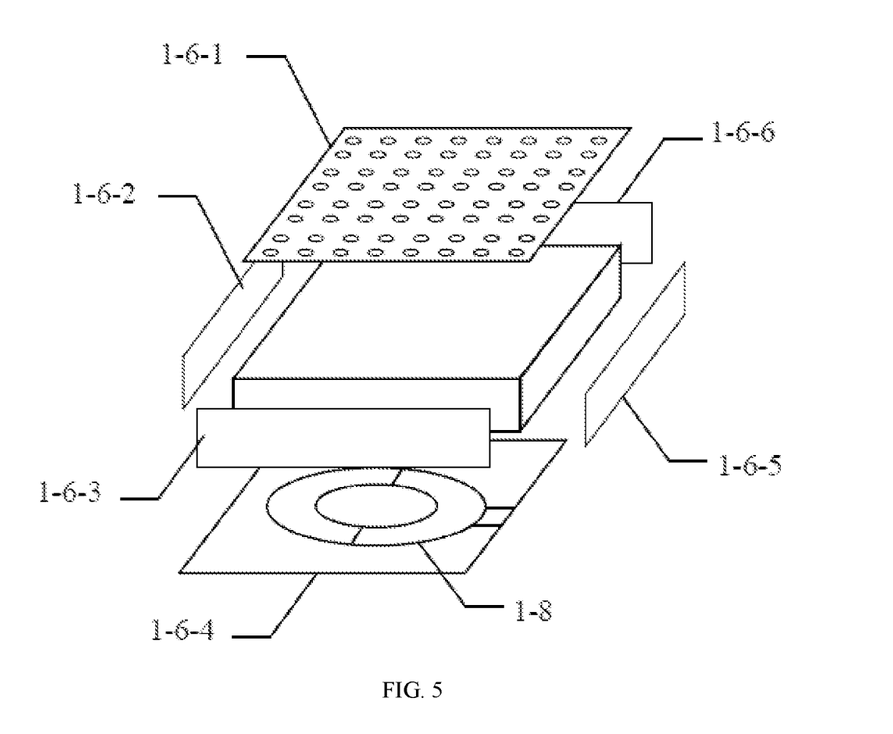
FIG. 5 is a schematic structural diagram illustrating a special PD set.

In reference to FIG. 5, the special PD set 1-6 includes four 1 mm*8 mm PDs and two 8 mm*8 mm PDs. The four 1 mm*8 mm PDs are a PD 1-6-2, a PD 1-6-3, a PD 1-6-5, and a PD 1-6-6 that are respectively located on a left surface, a front surface, a right surface, and a rear surface of the special PD set 1-6. The two mm*8 mm PDs are a porous PD 1-6-1 and a PD 1-6-4 on a bottom surface of the special PD set 1-6. The front porous PD 1-6-1 is provided with 64 holes with a diameter of 0.5 mm, and each hole corresponds to one nitrogen atom injection position, namely, the NV centers 1-9-2, in the special diamond. The thin cooper wire ring-shaped antenna 1-8 is attached on a surface of the bottom PD 1-6-4. The NV centers 1-9-2 in the special diamond are excited by 532 nm laser light to produce 600-800 nm fluorescence. The Zeeman splitting occurs under the function of magnetic field, and the ODMR signal is performed when the ring-shaped antenna 1-8 is connected to the microwave source 7 to evenly radiate electromagnetic waves with the sweeping frequency including to Zeeman splitting. A surface, close to the special diamond, of each of the six PDs is attached with a filter in the filter set 1-7 to pass light within a wavelength of 600-800 nm, so that the PD only accepts the 600-800 nm fluorescence excited by the NV centers. The six PDs are attached on various surfaces of the special diamond to wrap the special diamond, and are configured to collect and absorb all the fluorescence excited by the special diamond, to greatly improve collection efficiency, convert a collected light signal into an electrical signal, and send the electrical signal to the high-speed data collection card 5. Then the high-speed data collection card 5 transmits the electrical signal to the computer 8. Finally, the computer 8 performs data processing, simulates, analyzes, amplifies, and filters the collected electrical signal, and then obtains a strength diagram of a measured cardiac magnetic field by drawing, based on strength of an electrical signal measured in each position and the corresponding position, the electrical signal in each position in the computer.

Figure 6:
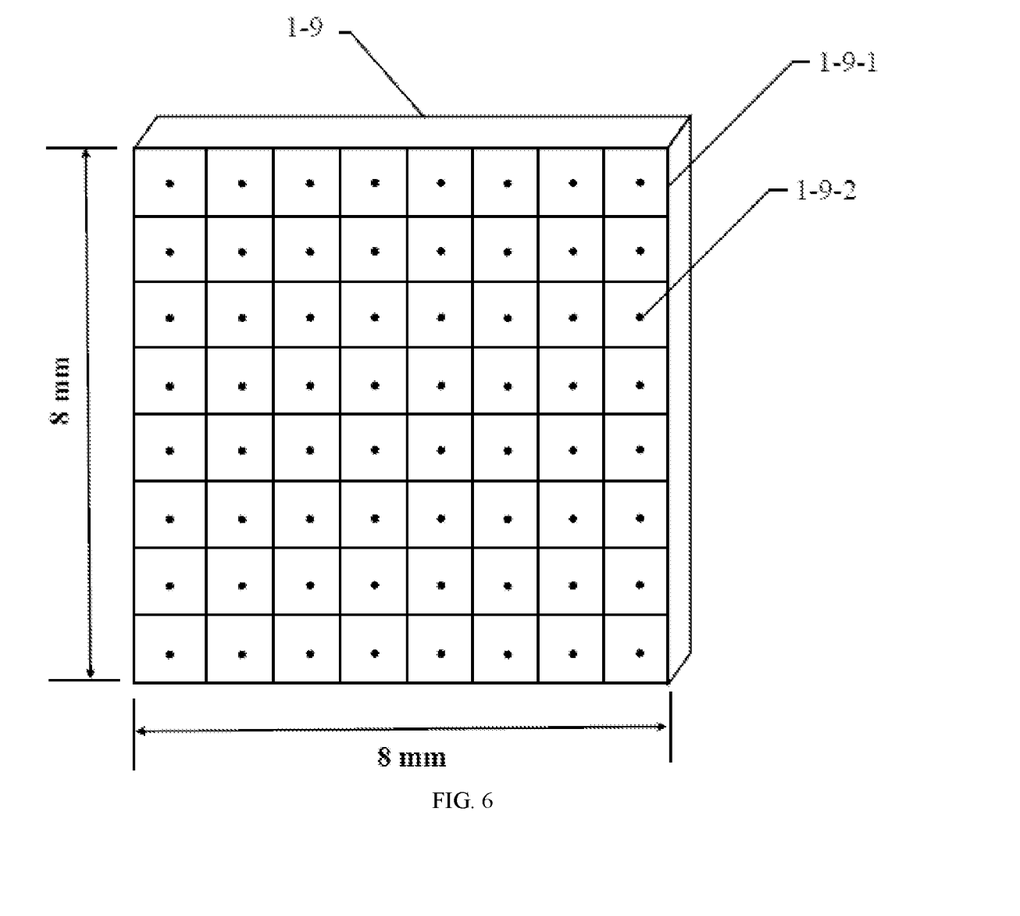
FIG. 6 is a schematic structural diagram illustrating special diamond.

In reference to FIG. 6, the special diamond 1-9 is an 8 mm*8 mm*1 mm cuboid block-shaped diamond, and is divided into 64 1 mm*1 mm*1 mm small unit blocks 1-9-1. In a process of preparing the NV centers in the special diamond, a mask injection process is used. That is, a layer of coating is covered on the front surface of the special diamond, and a circular hole (with a diameter of 0.2 mm) is formed in the center of each square small unit block, so that only the center of each small unit block is injected with nitrogen atoms to produce the NV centers 1-9-2 for fluorescence excitation of the array probe for cardiac magnetic field measurement.

Figure 7:
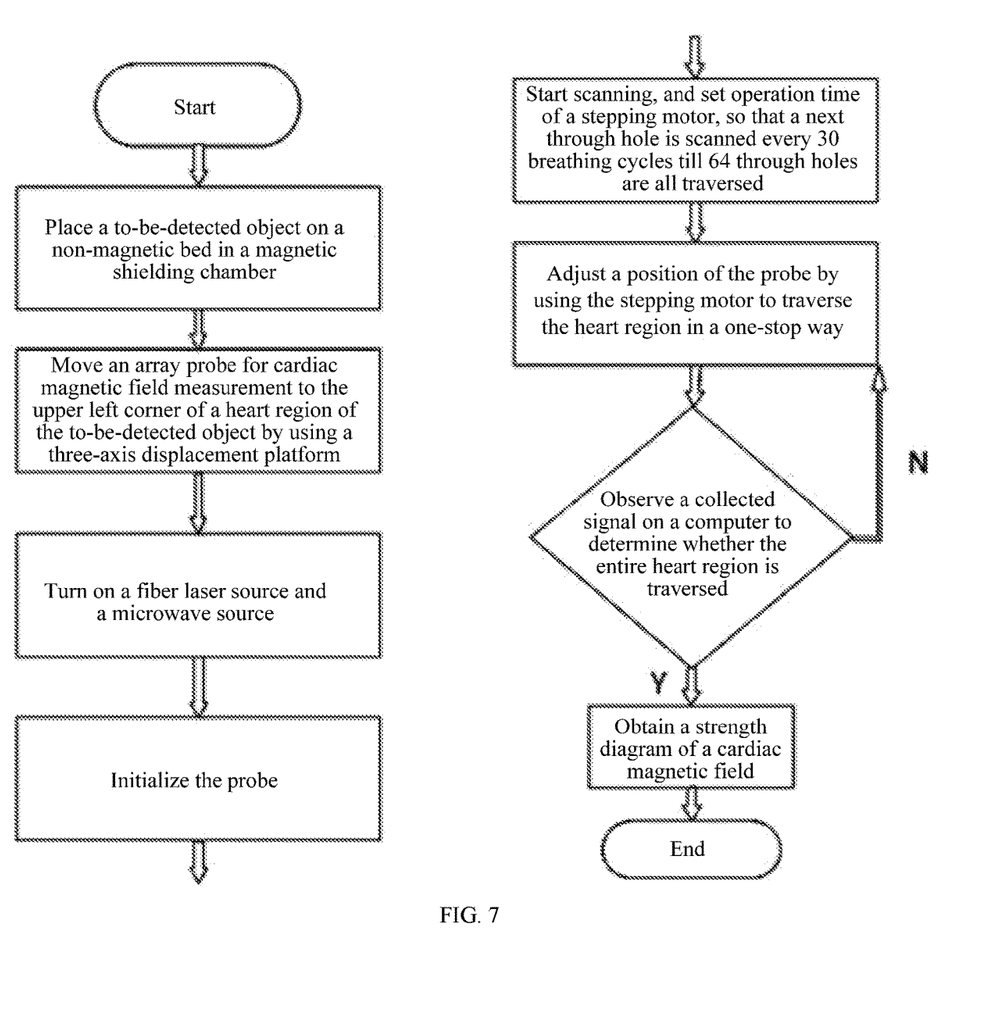
FIG. 7 is an operational flowchart illustrating operation of a cuboid magnetometer with high fluorescence collection efficiency, used for cardiac magnetic field measurement, and based on NV centers in diamond, and a cardiac magnetic field measurement system.

FIG. 7 is an operational flowchart illustrating operation of the apparatus. A to-be-detected object is placed on the non-magnetic bed 3 in the magnetic shielding chamber 4. The array probe 1 for cardiac magnetic field measurement is moved to the upper left corner of a heart region of the to-be-detected object by using the three-axis displacement platform 2, and is in contact with the skin. The fiber laser source 6 and the microwave source 7 are turned on, and the probe 1 is initialized. Scanning is started, and operation time of the stepping motor 1-2 is set. A next through hole 1-4-1 is scanned every 30 breathing cycles till 64 through holes are all traversed. The three-axis displacement platform 2 is used to adjust a position of the probe to traverse the heart region in a one-stop way. Signals collected by the special PD set 1-6 are transmitted to the high-speed data collection card 5. The collected signals are observed on the computer 8 to determine whether the entire heart region is traversed. If the signals of the heart region are completely displayed on the computer, the traversal is completed and a strength diagram of a cardiac magnetic field is obtained.

Although the embodiments of the present disclosure have been described, it should be understood that those of ordinary skill in the art may make various changes, modifications, replacements and variations to the above embodiments without departing from the principle and spirit of the present disclosure.

What is claimed is:

1. A magnetometer used for cardiac magnetic field measurement and based on nitrogen-vacancy (NV) centers in diamond, comprising: an array probe (1) for cardiac magnetic field measurement, a fiber laser source (6), and a microwave source (7), wherein the array probe (1) for cardiac magnetic field measurement comprises a non-magnetic shell (1-1), and a stepping motor (1-2), a porous rotary fiber coupling apparatus, a fiber bundle set (1-5), a special photodetector (PD) set (1-6), a ring-shaped antenna (1-8), and special diamond (1-9) that are all located in the non-magnetic shell (1-1); the porous rotary fiber coupling apparatus comprises a rotating disk (1-3) and a chassis (1-4); the rotating disk (1-3) is made of a non-magnetic material, and is provided with a laser through hole for connecting to a laser fiber, and the rotating disk (1-3) is connected to an output shaft of the stepping motor (1-2); the chassis (1-4) is made of the non-magnetic material, and is provided with m through holes (1-4-1) that form a circle; the m through holes (1-4-1) are equally spaced, positions of the through holes (1-4-1) correspond to a position of the laser through hole (1-3-1) on the rotating disk (1-3), and the m through holes (1-4-1) each are used to connect to one end of one of m fibers in the fiber bundle set (1-5); the special diamond (1-9) is divided into a total of m small unit blocks (1-9-1), a layer of coating is covered on a front surface of the special diamond, and a hole is formed in the center of each small unit block (1-9-1), so that the center of each small unit block is injected with nitrogen atoms to produce NV centers; the special PD set (1-6) comprises a PD attached on each surface of the special diamond (1-9), a PD (1-6-1) attached on the front surface of the special diamond (1-9) is provided with m holes, each hole corresponds to one nitrogen atom injection position in the special diamond, and the other end of each of them fibers is connected to one of the m small unit blocks through one of the m holes on the front PD (1-6-1); and the ring-shaped antenna (1-8) is attached on a surface of one of the other PDs, and the ring-shaped antenna (1-8) is connected to the microwave source (7).

2. The magnetometer used for cardiac magnetic field measurement and based on NV centers in diamond according to claim 1, wherein the array probe (1) for cardiac magnetic field measurement further comprises a filter set (1-7), a surface, in contact with the special diamond, of each PD in the special PD set (1-6) is attached with a filter in the filter set (1-7), and a front filter (1-7) is also provided with m holes.

3. The magnetometer used for cardiac magnetic field measurement and based on NV centers in diamond according to claim 2, wherein each small unit block (1-9-1) of the special diamond is provided with a fiber collimator (1-5-1), and the other end of each of the m fibers is connected to the fiber collimator (1-5-1).

4. The magnetometer used for cardiac magnetic field measurement and based on NV centers in diamond according to claim 3, wherein the fiber collimator (1-5-1) is provided with a convex lens (1-5-2).

5. The magnetometer used for cardiac magnetic field measurement and based on NV centers in diamond according to claim 3, wherein a bottom surface of the rotating disk (1-3) is provided with a convex point, and a top surface of the chassis (1-4) is provided with a concave point matching the convex point.

6. A cardiac magnetic field measurement system, comprising a three-axis displacement platform (2), a non-magnetic bed (3), a magnetic shielding chamber (4), a high-speed data collection card (5), and a computer (8), wherein the system further comprises the magnetometer according to claim 1; and the special PD set (1-6) in the magnetometer is connected to the high-speed data collection card (5), and the high-speed data collection card (5) is connected to the computer (8).

7. The cardiac magnetic field measurement system according to claim 6, wherein the array probe (1) for cardiac magnetic field measurement further comprises a filter set (1-7), a surface, in contact with the special diamond, of each PD in the special PD set (1-6) is attached with a filter in the filter set (1-7), and a front filter (1-7) is also provided with m holes.

8. The cardiac magnetic field measurement system according to claim 7, wherein each small unit block (1-9-1) of the special diamond is provided with a fiber collimator (1-5-1), and the other end of each of the m fibers is connected to the fiber collimator (1-5-1).

9. The cardiac magnetic field measurement system according to claim 8, wherein the fiber collimator (1-5-1) is provided with a convex lens (1-5-2).

10. The cardiac magnetic field measurement system according to claim 8, wherein a bottom surface of the rotating disk (1-3) is provided with a convex point, and a top surface of the chassis (1-4) is provided with a concave point matching the convex point.

* * * * *

UNITED STATES PATENT AND TRADEMARK OFFICE
CERTIFICATE OF CORRECTION

| | | |
|---|---|---|
| PATENT NO. | : 11,678,826 B2 | Page 1 of 1 |
| APPLICATION NO. | : 17/327671 | |
| DATED | : June 20, 2023 | |
| INVENTOR(S) | : Zongmin Ma et al. | |

It is certified that error appears in the above-identified patent and that said Letters Patent is hereby corrected as shown below:

On the Title Page

(73) Assignee
Please delete "North Univeristy of China" and insert --North University of China--.

Signed and Sealed this
Eighteenth Day of July, 2023

Katherine Kelly Vidal
*Director of the United States Patent and Trademark Office*